United States Patent [19]

Spiering et al.

[11] Patent Number: 6,114,683
[45] Date of Patent: Sep. 5, 2000

[54] PLANT CHLOROPHYLL CONTENT IMAGER WITH REFERENCE DETECTION SIGNALS

[75] Inventors: Bruce A. Spiering; Gregory A. Carter, both of Long Beach, Miss.

[73] Assignee: The United States of Ameria as represented by the Administrator of the National Aeronautics and Space Administration, Washington, D.C.

[21] Appl. No.: 09/033,129

[22] Filed: Mar. 2, 1998

[51] Int. Cl.$^7$ .................................. H01J 40/14
[52] U.S. Cl. ............................... 250/208.1; 250/559.4; 250/339.11
[58] Field of Search .................. 250/208.1, 559.4, 250/339.15, 339.1, 339.11, 339.12, 554, 461.1, 461.2; 356/400, 416, 417

[56] References Cited

U.S. PATENT DOCUMENTS

| | | | |
|---|---|---|---|
| 4,101,767 | 7/1978 | Lennington et al. | 250/339 |
| 4,204,950 | 5/1980 | Burford et al. | 209/558 |
| 4,225,242 | 9/1980 | Lane | 356/407 |
| 4,295,042 | 10/1981 | Wantanabe et al. | 250/226 |
| 4,650,336 | 3/1987 | Moll | 356/417 |
| 4,804,850 | 2/1989 | Norrish et al. | 250/459 |
| 5,014,225 | 5/1991 | Vidaver et al. | 365/550 |
| 5,035,472 | 7/1991 | Hansen et al. | 350/1.1 |
| 5,353,053 | 10/1994 | Nishioka et al. | 348/33 |
| 5,389,781 | 2/1995 | Beck et al. | 250/226 |
| 5,394,237 | 2/1995 | Chang et al. | 356/328 |
| 5,412,219 | 5/1995 | Chapplle et al. | 250/464.1 |
| 5,467,271 | 11/1995 | Abel et al. | 364/420 |
| 5,486,915 | 1/1996 | Jeffers et al. | 356/318 |
| 5,525,801 | 6/1996 | Jackensen et al. | 250/352 |
| 5,576,550 | 11/1996 | Koppikar | 250/459.1 |
| 5,606,821 | 3/1997 | Sajadi et al. | 47/1.7 |
| 5,677,532 | 10/1997 | Duncan et al. | 250/339.15 |
| 5,677,761 | 10/1997 | Hasson | 250/339.15 |
| 5,900,942 | 5/1999 | Spiering | 356/400 |

FOREIGN PATENT DOCUMENTS 62-282245 12/1987 Japan.

OTHER PUBLICATIONS

Carter, G., "Ratios of Leaf Reflectances in Narrow Wavebands as Indicators of Plant Stress", *Int. J. Remote Sensing*, vol. 15, No. 3, 679–703, (1994) (Month Unknown).

Carter, G., et al., "Early Detection of Plant Stress by Digital Imaging Within Narrow Stress–Sensitive Wavebands", *Remote Sens Environ 50*, —295–302, (1994) (Month Unknown).

Carter, G., et al., "Leaf Optical Properties in Liriodendron Tulipifera and Pinus Strobus as Influenced by Increased Atmospheric Ozone and Carbon Dioxide", *Can. J. For. Res.* 25, 407–412, (1995) (Month Unknown).

(List continued on next page.)

*Primary Examiner*—Que T. Le
*Attorney, Agent, or Firm*—Diana M. Cox; Beth A. Vrioni; Gary G. Borda

[57] ABSTRACT

A portable plant chlorophyll imaging system is described which collects light reflected from a target plant and separates the collected light into two different wavelength bands. These wavelength bands, or channels, are described as having center wavelengths of 700 nm and 840 nm. The light collected in these two channels is processed using synchronized video cameras. A controller provided in the system compares the level of light of video images reflected from a target plant with a reference level of light from a source illuminating the plant. The percent of reflection in the two separate wavelength bands from a target plant are compared to provide a ratio video image which indicates a relative level of plant chlorophyll content and physiological stress. Multiple display modes are described for viewing the video images.

19 Claims, 4 Drawing Sheets

OTHER PUBLICATIONS

Carter, G., et al., "Narrow–Band Reflectance Imagery Compared With Thermal Imagery for Early Detection of Plant Stress", *L. Plant Physiol.* vol. 148, 515–522, (1996) (Month Unknown).

Carter, G., et al., "Spectral Reflectance Characteristics and Digital Imagery of a Pine Needle Blight in the Southeastern United States", *Can. J. For. Res. 26,* 402–407, (1996), Month Unknown.

Carter, G.A., "Responses of Leaf Spectral Reflectance to Plant Stress", *American Journal of Botany,* 239–243, (Mar. 1993).

Cibula, W.G., et al., "Identification of Far–Red Reflectance Response to Ectomycorrhizae in Slash Pine", *Int. J. Remote Sensing,* vol. 13, No. 5, 925–932, (1992) (Month Unknown).

PLANT CHLOROPHYLL CONTENT IMAGER WITH REFERENCE DETECTION SIGNALS

The invention described herein was made by employee (s) of the United States Government and may be manufactured and used by or for the Government for Government purposes without the payment of any royalties thereon or therefor.

TECHNICAL FIELD OF THE INVENTION

The present invention relates generally to plant chlorophyll content detection and in particular the present invention relates to a device which visually images chlorophyll content in a plant using light reflectance.

BACKGROUND OF THE INVENTION

Early detection of vegetation physiological stress is beneficial to the environmental and agricultural business community. Plant stresses can be a result of numerous influences including but not limited to drought, chemicals such as herbicides, or biological influences. Early detection can provide an opportunity to reverse the physiological stress or at least identify that stress is present. When unfavorable growth conditions result in plant physiological stress, leaf chlorophyll content typically begins to decrease. Consequently, methods of detecting the content of leaf chlorophyll provide a measure or indication of a level of such stress.

Different approaches to plant stress detection by measuring leaf chlorophyll are available. One such technique which can be used is fluorescence. In the case of fluorescence, incident light is absorbed by leaf pigments. Not all of the absorbed light energy is transferred chemically to be used in photosynthesis. Rather, some of this absorbed energy is re-emitted, or fluoresced, by chlorophyll at far-red, or near-infrared wavelengths. Maximum chlorophyll fluorescence occurs at wavelengths near 690 and 730 nm. For this reason, fluorometers often measure fluorescence with narrow bands centered near 690 or 730 nm. In general, fluorescence in these bands tends to increase with decreased chlorophyll content or increased degree of physiological stress. To measure far-red or near-infrared fluorescence, the leaf is irradiated only with light of much shorter wavelengths (e.g., blue or green light). This insures that any far-red or near-infrared light emanating from the leaf is indeed fluorescence and not merely incident light that has been reflected by the leaf.

A second method of measuring plant chlorophyll content is through the use of transmittance. This technique transmits light through a leaf of a target plant. A percent of light transmitted through the leaf at specific wavelengths is measured. These wavelengths are typically 650 nm and 940 nm. As chlorophyll content changes, the ratio of transmittance at these wavelengths changes. A clear defect in monitoring plant chlorophyll content using this method is the requirement of physical contact with a plant leaf.

Another approach to detecting physiological plant stress by measuring leaf chlorophyll is accomplished by monitoring the reflection of incident light. Reflectance of incident radiation from the leaf interior increases as plant chlorophyll decreases, providing an optical indicator of stress. Reflectance sensitivity analysis has shown that increased reflectance in specific wavebands provides an early and more consistent indication of stress than reflectance at other wavelengths as a result of the absorption properties of chlorophyll. Depending on the severity of stress, this reflectance response can be detected prior to damage symptoms apparent to the unaided eye. Reflectance has been shown to detect decreased chlorophyll content by at least sixteen days prior to visual indications such as leaf color changes. Reflectance measurements are typically made while the plant leaf is exposed to a full incident spectrum from the sun, or an artificial light source. Although some fluoresced energy must also be measured in combination with reflected light, the fluoresced energy is small compared with a greater intensity of reflected light. Further, physical contact with the target plant is not required.

Different techniques are known for conducting reflectance measurements to indicate plant stress. These techniques, however, require extensive field measurements combined with laboratory analysis of the collected measurements. For the reasons stated above, and for other reasons stated below which will become apparent to those skilled in the art upon reading and understanding the present specification, there is a need in the art for a portable video imager for detecting plant chlorophyll levels for providing an indication of physiological stress in plants based on reflectance of incident light.

SUMMARY OF THE INVENTION

The above mentioned problems with detecting plant stress and other problems addressed by the present invention will be understood by reading and studying the following specification. A portable video imager is described which uses reflected light from a target plant area at two wavelengths of light to detect chlorophyll content and provide an indication of plant stress.

A chlorophyll content imaging system is described in one embodiment. The imaging system comprises an optical system providing at least two video output signals. A first video signal is filtered to have a first central wavelength of transmission, and a second video signal is filtered to have a second central wavelength of transmission. The imaging system includes first and second light detectors for detecting a light source and providing first and second reference signals, and a controller for receiving the first and second video output signals and providing an output video signal indicating a relative chlorophyll content of target vegetation. The controller provides an image of a percent of light reflected from the target vegetation by comparing the first and second video signals produced from light reflected from the target plant against outputs from the first and second reference signals.

In another embodiment, a portable light reflectance video system for use in imaging plant chlorophyll content comprises an optical lens for collecting light reflected from a target plant under test, and an optical beam splitter for dividing light collected by the optical lens into first and second light beams. A first optical bandpass filter is provided for receiving the first light beam from the optical beam splitter and providing a first light output having a center wavelength of approximately 700 nm. A first video camera provides a first video signal in response to the first light output having a center wavelength of approximately 700 nm. A second optical bandpass filter receives the second light beam from the optical beam splitter and provides a light output having a center wavelength of approximately 840 nm. A second video camera provides a second video signal in response to the second light output having a center wavelength of approximately 840 nm. First and second light detectors are included for detecting a light source and providing first and second reference signals. The system includes a processor for providing an output video signal indicating plant chlorophyll content levels as a ratio of the percent of reflected light having a center wavelength of approximately 700 nm to the percent of reflected light having a center wavelength of approximately 840 nm. Finally, a display provides a user with a video image of the target plant to identify chlorophyll content.

In yet another embodiment, a method of viewing plant chlorophyll content for identifying early plant stress using a chlorophyll content imager is provided. The method comprises the steps of detecting light from a light source having a first wavelength, detecting light from the light source having a second wavelength, and providing a first video image of light reflected from a target plant having the first wavelength. A second video image is provided of light reflected from the target plant having the second wavelength. The method also includes the steps of providing a third video image of a first reflected percent of light reflected from the target plant having the first wavelength from the light detected from the light source having the first wavelength, and providing a fourth video image of a second reflected percent of light reflected from the target plant having the second wavelength from the light detected from the light source having the second wavelength. A fifth video image is provided and displayed as a ratio of the third video image to the fourth video image using the chlorophyll content imager.

DETAILED DESCRIPTION OF THE INVENTION

In the following detailed description of the preferred embodiments, reference is made to the accompanying drawings which form a part hereof, and in which is shown by way of illustration specific preferred embodiments in which the inventions may be practiced. These embodiments are described in sufficient detail to enable those skilled in the art to practice the invention, and it is to be understood that other embodiments may be utilized and that logical, mechanical and electrical changes may be made without departing from the present inventions. The following detailed description is, therefore, not to be taken in a limiting sense, and the scope of the present invention is defined only by the appended claims.

Figure 1:
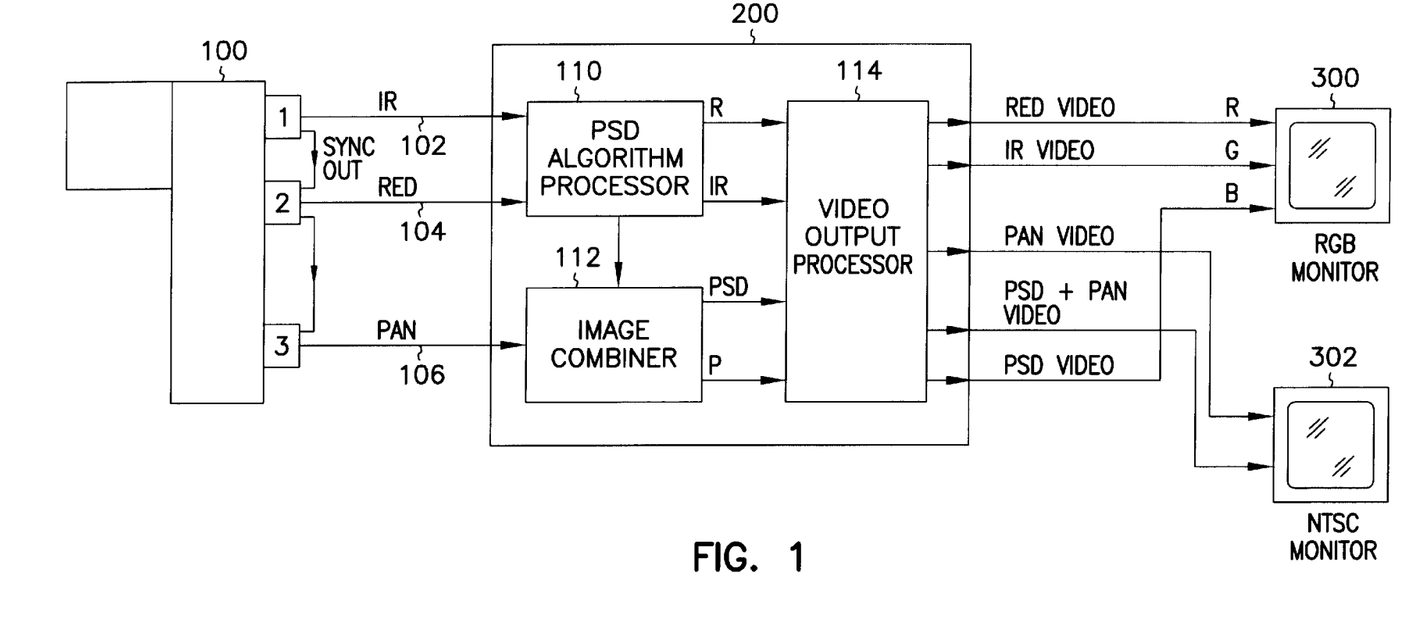
FIG. 1 is a schematic diagram of a portable video imager of the present invention using light reflectance.

Referring to FIG. 1, one embodiment of a portable video imager system of the present invention for detecting chlorophyll levels is described. The video imager system processes light reflected from plants in two different wavelength bands and compares the amount of light from these two bands to provide a video image of a plant target area. The system compares the level of light reflected from a target plant in the two bands with a reference level of light in the two bands from a source illuminating the plant. The system provides a video output indicating chlorophyll content levels, as an indication of the relative plant stress level. The detection system is preferably embodied as a portable unit so that it can be used by an operator in the field for real time analysis of the condition of plants.

The video imager system includes a three channel multispectral optic system 100 which collects light from a target area. The multispectral optic system includes a first light filter, having a wavelength in the range of 840±5 nm, to pass light through to a video camera. The multispectral system also includes a second light filter having a wavelength in the range of 695±5 nm, to pass light through to a second video camera Finally, a third image is provided is by a third camera. The third image is unfiltered. The outputs 102, 104 and 106 of the cameras are provided to processor 200 which provides a variety of video outputs to monitors 300 or 302. The processor includes an algorithm processor 110, an image combiner 112 and an image multiplexor 114.

The present system provides several display modes which are described herein. The system is implemented using the RS-170 video standard. The RS-170 format is not a requirement to produce the PSD Signal described below. However, if RS-170 is not used in the input signal, circuitry would have to be added to produce the RS-170 format for image display on RS-170 or NTSC format monitors. If a computer system is used to digitize the PSD Signal and produce the display modes, then additional circuitry may not be required. If the entire system is converted to a digital implementation, the algorithm for computing the plant stress ratio remains the same, as would the algorithms used to create the display presentations. The RS 170 implementation was chosen for availability of low cost cameras and monitors.

Figure 2:
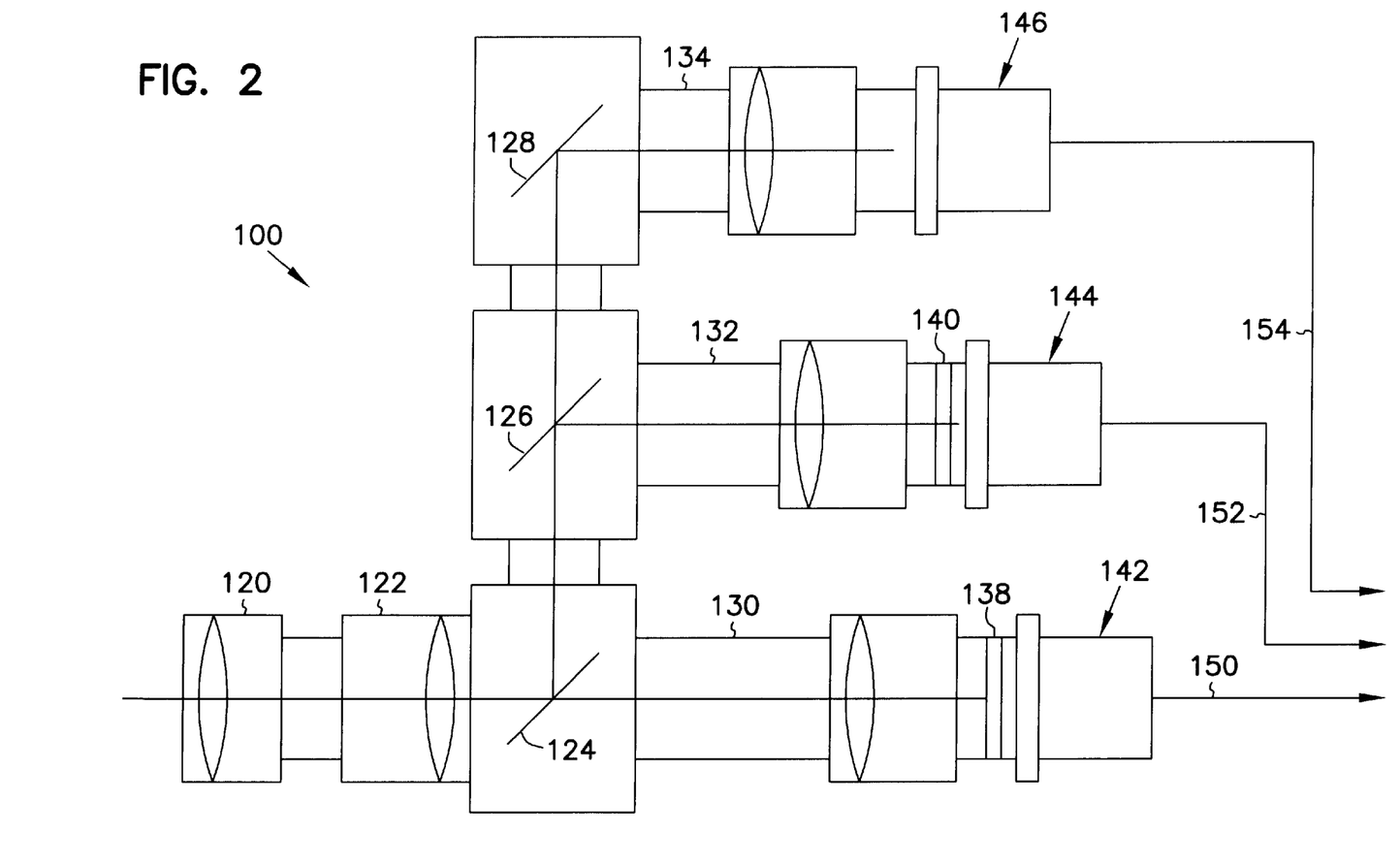
FIG. 2 illustrates an imaging system of FIG. 1.

Three video cameras are configured in the multispectral optical system 100 to obtain three spatially co-registered images with appropriate optical bandpass filters installed. Referring to FIG. 2, a detailed description of one embodiment of the multispectral imaging system 100 is described. The multi spectral imaging system 100 is illustrated for generating a plurality of co-registered images. The system 100 employs first, second and third CCD video cameras 142, 144 and 146, each of which detects an image of an object, and generates an electrical representation thereof. Although the use of CCD video cameras is preferred, it will of course be understood that any other type of two-dimensional imaging device or detector may be employed. The system 100 includes a primary lens assembly having a focusing lens 120. The focusing lens 120 focuses an incoming image beam, thereby forming a real image of the object. The primary lens assembly is connected to a collimating lens 122 which re-expands or collimates the projected object image into a collimated image beam that is directed into a beam splitter assembly.

The beam splitter assembly includes first and second beam splitters 124 and 126 for splitting the collimated image beam into first, second, third and fourth image beams. The first image beam is a version of the image beam which is transmitted through the first beam splitter to camera 142. The second image beam is reflected off of the first beam splitter 124 at a 90° angle. The third image beam is reflected off of the second beam splitter 126 as a reversed version of the second image beam, and is thus a twice reflected version of the original collimated image beam 29. The third image is transmitted to camera 144. The fourth image beam is the portion of the second image beam which is transmitted through the second beam splitter 126. A fold mirror 128 reflects the fourth image beam at a 90° angle, thereby generating a fifth image beam which, having also been twice reflected, is of the same orientation as the original collimated image beam. The fold mirror 128 is thus necessary to restore the object image to its correct orientation since the second and fourth image beams constitute once reflected, and therefore reversed, versions of the object image beam.

First, second and third lens tubes 130, 132 and 134 are provided for directing the first, third and fifth image beams, respectively, to the corresponding CCD cameras 142, 144 and 146 The length of each of the tubes is selected to provide the total image beam path length which is necessary to provide co-registered images of the object to each of the cameras. Disposed along the image directed to cameras 142 and 144 are first and second filters 138 and 140, respectively. Each filter provides selective wavelength filtering of the received images. The filters are bandpass filters which pass only a single wavelength or small range of wavelengths. It should be noted that the filters could be located anywhere along the paths of the first and third image beams. Filter 138 is preferably a 700±5 nm filter, and filter 140 is preferably an 840±5 nm filter.

While a typical beam splitter transmits a percentage of an incoming beam equal to the percentage of the reflected beam in a 50/50 ratio, other ratios can also be employed. In addition, although beam splitters are generally independent of wavelength, a dichroic mirror can also be employed in the beam splitters 124 and 126 which are wavelength specific as to reflectance and transmittance. Thus, with a dichroic mirror, all of a first range of wavelengths may be transmitted, while all of a second, different range of wavelengths may be reflected so that no energy is lost in the beam splitting process for the specific wave band. The use of dichroic mirrors can therefore serve the same purpose as the filters 138 and 140.

To provide images for plant stress analysis, the first filter 138 is selected to be a narrow bandpass filter which passes only light of 700 nm wavelength to the CCD array in the first camera 142. As discussed previously, light at 700 nm is absorbed by chlorophyll in the plant. Since plant stress often causes a reduction in chlorophyll production, a variation in the plant's absorption, and thus reflectance, of 700 nm wavelength light is frequently an indicator of plant stress. However, the amount of light reflected at this wavelength will also vary in response to various environmental conditions, such as ambient light intensity. Thus, a reference wavelength must also be imaged which is not responsive to chlorophyll production in the plant. In this instance, an infra-red wavelength, such as 840 nm, can be employed as a reference, and thus, the second filter 140 is selected to be a narrow bandpass filter which passes only 840 nm wavelength light to the CCD array in the second camera 144. Finally, the third camera 146 provides a visible image which can be overlaid with the images generated by the first and second cameras to facilitate a visual observation of the plant stress measurements.

The image signals generated by each of the cameras are passed to a suitable image processing system which performs the necessary comparison of the chlorophyll production responsive image generated by the first camera and the reference image generated by the second camera, and generates a visual indication of plant stress which is overlaid with the visual spectrum image generated by the third camera. It should be understood that the multispectral system 100 insures automatic co-registration of the three images and reduces the amount of data processing which must be carried out to correlate each pixel of each image.

Figure 3A:
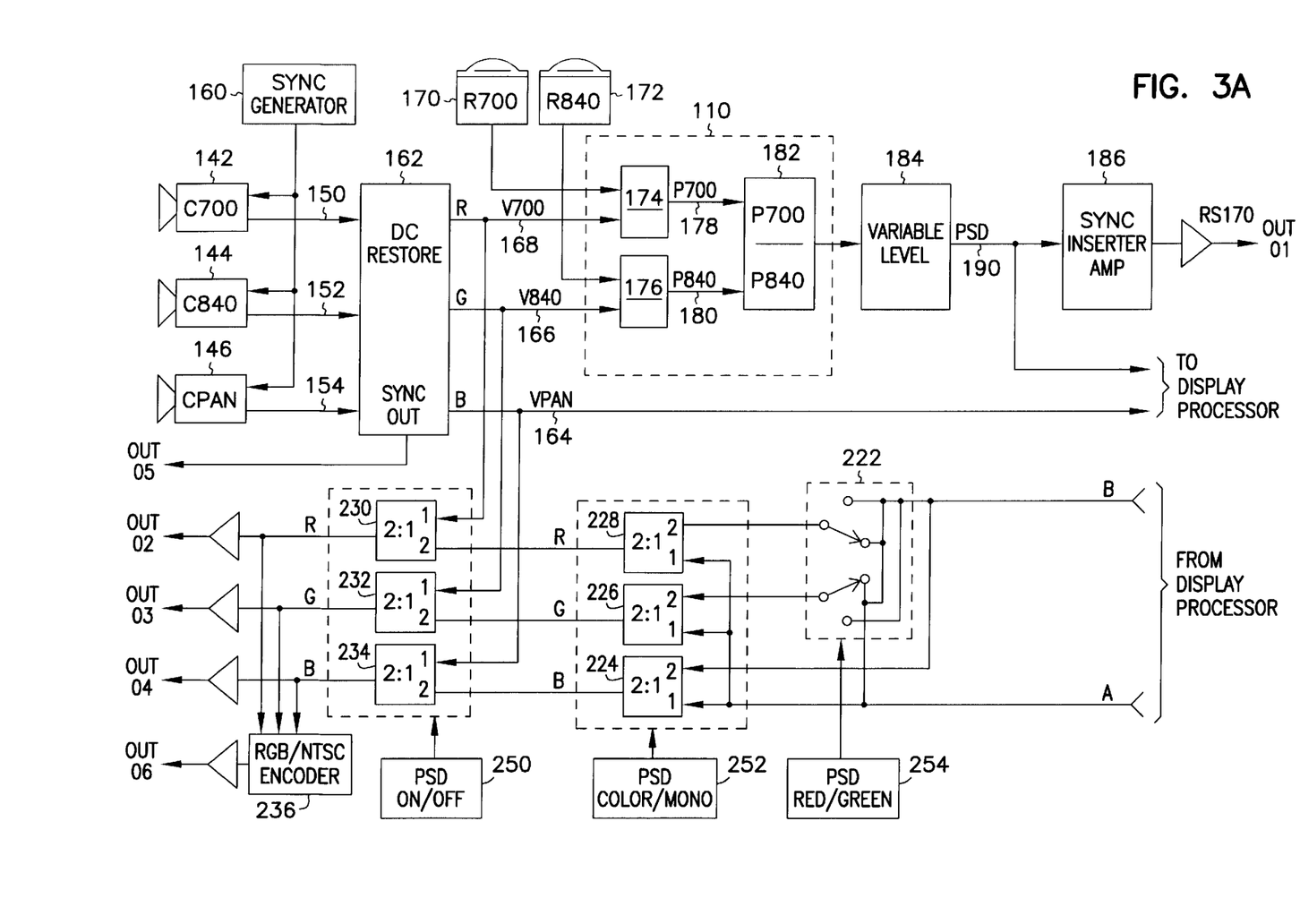
FIGS. 3A and 3B are block diagrams of the processing system of FIG. 1.
Figure 3B:
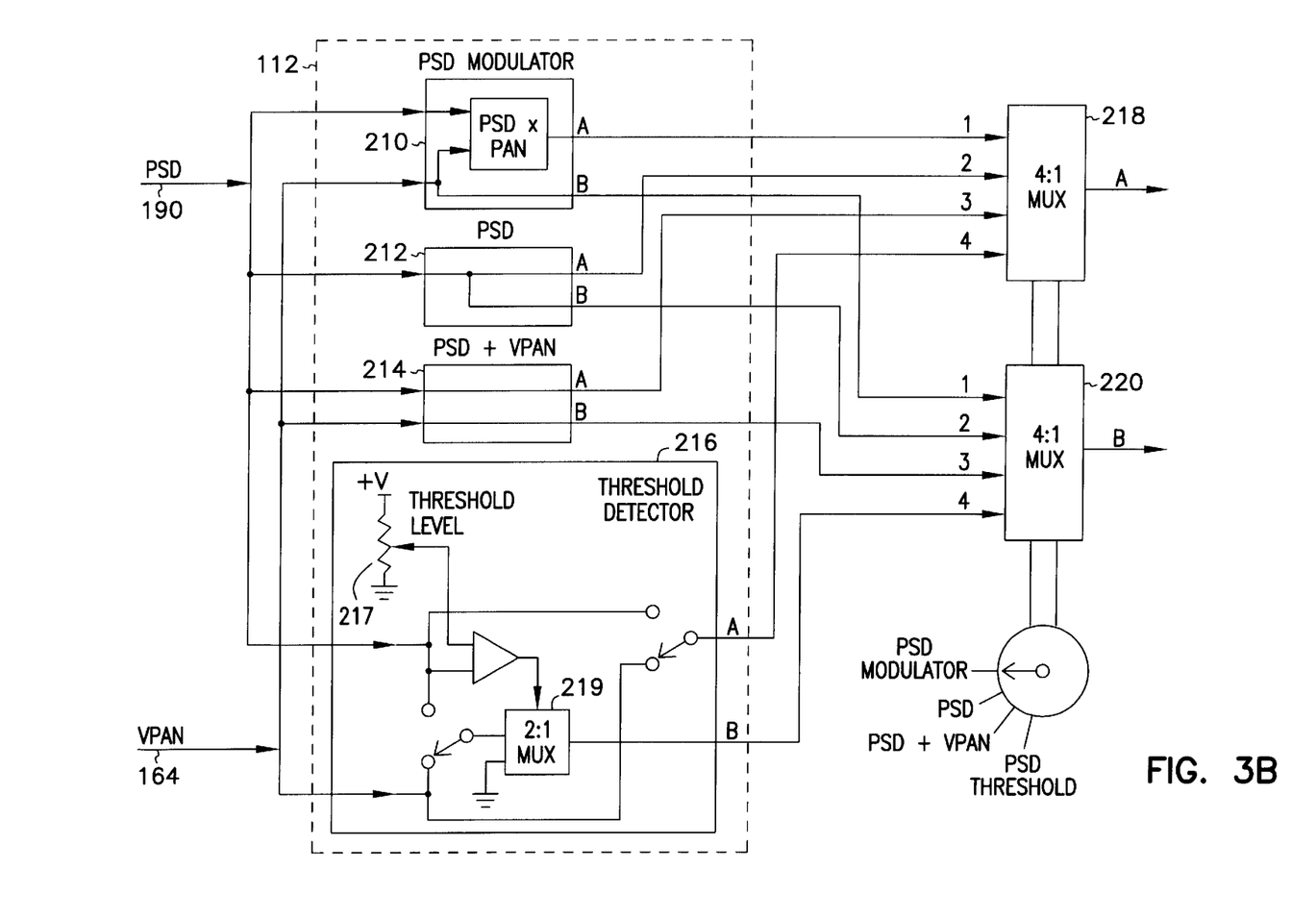

Referring to FIGS. 3A and 3B, a more detailed description of the processor 200 is provided. An RS-170 synchronize generator 160 is coupled to the video cameras 142, 144 and 146 to provide synchronizing signals which produce temporally co-registered images on camera outputs 150, 152 and 154. The RS-170 format video signals from the three cameras are sent to a DC Restore system 162 where all of the video signals are referenced to zero volts and a new sync signal (Sync Output) is extracted. The Sync Output signal is used in the sync inserter circuit 186 for display of the computed PSD (Plant Stress Detection) signal 190. The Sync Output signal is also coupled to the RGB to NTSC Encoder 236, and is provided as an output to sync RGB monitor 300.

The three signals output from the DC Restore circuit 162 are routed to the algorithm processor 110 (V700, V840 and VPAN). The outputs are also coupled to outputs 02, 03, 04 and 06 for display on RGB Monitor 300 or NTSC color monitor 302 thru PSD ON/OFF mux circuits 230–234. This display mode is used for alignment of the system only. That is, the multispectral optic system is aligned while viewing the three images simultaneously on a monitor.

Signal 168, which corresponds to the video camera filtered at 700 nm, and signal 166, which corresponds to the video camera filtered at 840 nm, are sent to the PSD Processor 110. The PSD Analog Processor performs the plant stress detection algorithm. Output signals from two discrete silicon photo diode detectors 170 and 172 are used as light references. The detectors are covered by one each of the same optical bandpass filters used on the video cameras. That is, detector 170 provides a reference centered at 700 nm, and detector 172 provides a reference centered at 840 nm (R700 and R840). The filters are covered by diffuse ground glass providing an unfocused wide field of view. The reference sensors are placed so that they can view the entire (approximately) sky while the video signals are being processed. The output signals from the photo diodes are sent to the PSD Processor 110. The processor computes the percent reflectance in each pass band and then takes the ratio of the two percent reflectance to produce the plant stress ratio. Referring to FIGS. 3A and 3B, signal 168 (V700) is divided by the reference output of detector 170 (R700) to produce output 178 of divider circuit 174. The output, P700, is the percent of 700 nm reflected light. Output 166 (V840) is divided by the reference output (R840) of detector 172 to produce output 180 of divider circuit 176. The output, P840, is the percent of 840 nm reflected light. Output signal 178 is divided by signal 180 to produce the plant stress ratio signal (PSD) as an output of divider circuit 182. This signal indicates a relative chlorophyll level by calculating the ratio of the percent of 700 nm reflected light to the percent of 840 nm reflected light.

The ratio of percent reflectance for the two video wavelengths ranges from approximately 0.1 for a healthy plant to 0.4 and greater for an unhealthy plant. It will be understood that these ratios can vary for different plant species. As such, a ratio below 0.2 generally indicates a healthy plant, while a ratio above 0.25 generally indicates an unhealthy plant.

The PSD signal is coupled to a variable level circuit 184 for adjusting a bias of the signal. The PSD signal is also coupled to a sync inserter/amplifier/buffer 186 for direct output on Out 01 connection for direct viewing or digitization. The PSD Signal is also sent to display processor circuitry where it is used to create four different display modes.

The display circuitry 112 produces four different presentations of the PSD signal. These results can be switched from color to monochrome via the color/Mono switch 252 to control multiplex circuits 224–228. When mono is selected, input 2 of the multiplex circuits is coupled to the respective outputs. When color is on, input 1 is coupled to the multiplex circuit outputs and the display color can be switched between red or green with the Red/Green switch 254 which controls switching circuit 222. Thus, green is provided when multiplex circuit 226 is coupled to multiplex circuit 220.

Likewise, red is provided when multiplex circuit 228 is coupled to multiplex circuit 220.

The four different video presentation modes are described below. The first mode is a PSD Modulator mode, illustrated by circuit 210. This mode multiplies the PSD signal 190 by the unfiltered video pan signal 164. The resulting output signal is sent to input 1 of the multiplex circuit 218. The video pan signal 164 is sent to input 1 of multiplex circuit 220. Thus, when input 1 is selected from multiplex circuits 218 and 220, the output of the multiplex circuits 218 and 220 are coupled through output processor 114 as selected.

A second video viewing option is a PSD mode illustrated at logic block 212. This mode simply outputs the PSD signal 190 from both multiplex circuits 218 and 220 via inputs 2. The output is the same on all colors, thereby producing a gray scale image or viewing.

A third video viewing option is referred to as PSD+Vpan and illustrated at block 14. This mode simply couples the PSD signal 190 to input 3 of multiplex circuit 218 and couples the video pan signal 164 to input 3 of multiplex circuit 220.

The final video viewing option is a PSD Threshold mode. This mode provides several output options of its own. The PSD Signal is sent to a Threshold Detector circuit 216 (comparator). A threshold voltage is set via a potentiometer 217. Whenever the PSD Signal 190 exceeds the set threshold voltage, the comparator switches a 2:1 multiplexer 219 between zero volts and either the PSD signal 190 or the pan signal 164, whichever is selected. This output is sent to input 4 of multiplex circuit 220. The input 4 to multiplex circuit 218 can be either the PSD signal 190 or pan signal 164. Thus, the threshold detector circuit compares the DSP signal to a predetermined voltage to identify regions of the PSD video signal which exceed an identified stress level, such as 0.25. In PSD color mode, the image above the threshold will appear bright (saturated) red or green. All the rest of the image will be a gray level of either the PSD Signal or video pan signal, whichever has been selected.

In operation, the chlorophyll content imager performs an analysis of the ratio of percent reflectance from two distinct wavelength channels, 700 and 840 nm. The system provides a video output which can be viewed to indicate plant chlorophyll levels. The multiplex and switching circuits described are useful in viewing the PSD signal in different modes. These modes, however, can be changed to suit the user's needs. Thus, the multiplex and switching circuits 114 can be changed without departing from the present invention.

The imager has been designed to allow a user to easily carry the system and view plant chlorophyll levels in a location where the plant is growing. As such, real-time analysis is possible. Further, physical contact with the plant is not necessary as with transmittance-based instrumentation. The present invention can be used by biologists or agriculturalists to assist in indicating any species of plant which may be suffering from stress due to a variety of causes. Although the present invention does not identify the cause of such stress, it is believed that early detection of plant stress provides options not available if plant stress is not detected until visual indications are present.

It will be appreciated by those skilled in the art that variations in the circuitry or construction of the chlorophyll content imager described herein are possible. For example, the video images can be digitized prior to performing the chlorophyll algorithm. Further, variations in the optical filter wavelengths are contemplated. The described center wavelengths of 700 and 840 nm, however, are preferred and believed to provide the best indication of early chlorophyll content loss. Further, although one collection lens 120 has been described, it will be appreciated that multiple collection lenses could be used in combination with separate bandpass filters to measure reflected light.

CONCLUSION

A portable plant chlorophyll imaging system has been described which collects light reflected from a target plant and separates the collected light into two different wavelength bands. These wavelength bands, or channels, are described as having center wavelengths of 700 nm and 840 nm. The light collected in these two channels is processed using video cameras. A controller provided in the system compares the level of light of video images reflected from a target plant with a reference level of light from a source illuminating the plant. The percent of reflection in the two separate wavelength bands from a target plant are compared to provide a ratio video image which indicates a relative level of plant physiological stress. Multiple display modes were also described for viewing the video images. A third video camera was described for providing an unfiltered image of the target vegetation.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is manifestly intended that this invention be limited only by the claims and the equivalents thereof.

What is claimed is:

1. A chlorophyll content imaging system comprising:
   an optical system having an input for receiving light reflected from target vegetation and providing a first video signal of the light reflected from the target vegetation that has been filtered to have a first central wavelength of transmission, and a second video signal of the light reflected from the target vegetation that has been filtered to have a second central wavelength of transmission;
   first and second light detectors for detecting light from a light source and providing first and second reference signals; and
   a controller for receiving the first and second video signals and providing an output video signal indicating a relative chlorophyll content of the target vegetation based on the first and second video signals and the first and second reference signals, the controller compares the first and second video signals respectively with the first and second reference signals, and wherein the relative chlorophyll content of the target vegetation is indicated as a ratio of a percent of the first video signal to the first reference signal and a percent of the second video signal to the second reference signal.

2. The chlorophyll content imaging system of claim 1 wherein the first central wavelength of transmission of the first video signal is 700 nm.

3. The chlorophyll content imaging system of claim 1 wherein the second central wavelength of transmission of the second video signal is 840 nm.

4. The chlorophyll content imaging system of claim 1 wherein the optical system comprises:
   a first video camera to provide the first video signal;
   a second video camera to provide the second video signal;

a third video camera to provide a third unfiltered video signal; and an optical light splitter system to provide light reflected from the target vegetation to the first video camera, second video camera and third video camera, wherein the first, second and third video signals are synchronized.

5. The chlorophyll content imaging system of claim 1 wherein the first and second light detectors provide first and second reference signals which are respectively filtered to have central wavelengths of transmission equal to the first and second central wavelengths of transmission of the first and second video signals.

6. The chlorophyll content imaging system of claim 5 wherein the first central wavelength of transmission is 700 nm, and the second central wavelength of transmission is 840 nm.

7. The chlorophyll content imaging system of claim 4 further comprising multiplex circuitry for providing the output video signal of the processor and the third video signal to a display monitor.

8. The chlorophyll content imaging system of claim 7 wherein the multiplex circuitry is configured to allow multiple modes of color and mono video display.

9. A portable light reflectance video system for use in imaging plant chlorophyll content comprising:

an optical lens for collecting light reflected from a target plant under test;

an optical beam splitter for dividing the light collected by the optical lens into first and second light beams;

a first optical bandpass filter for receiving the first light beam from the optical beam splitter and providing a first light output having a center wavelength of approximately 700 nm;

a first video camera for providing a first video signal in response to the first light output having a center wavelength of approximately 700 nm;

a second optical bandpass filter for receiving the second light beam from the optical beam splitter and providing a second light output having a center wavelength of approximately 840 nm;

a second video camera for providing a second video signal in response to the second light output having a center wavelength of approximately 840 nm;

first and second light detectors for detecting light from a light source and providing first and second reference signals;

a processor for providing an output video signal indicating plant chlorophyll content levels as a ratio of the percent of reflected light having a center wavelength of approximately 700 nm, determined by comparing the first video output signal and the first reference signal, to the percent of reflected light having a center wavelength of approximately 840 nm, determined by comparing, the second video output signal and the second reference signal; and a display for providing a user with a display of the output video signal.

10. The portable light reflectance video system of claim 9 further comprising a threshold detection circuit coupled to the processor for comparing the output video signal from the processor to a threshold level and generating a video signal.

11. The portable light reflectance video system of claim 9 further comprising a third video camera for providing a third unfiltered video signal of the target plant.

12. The portable light reflectance video system of claim 11 further comprising a multiplex circuit coupled to the processor, the display and the third video camera, the multiplex circuit provides video signals to the display selected from either the output video signal from the processor or the third unfiltered video signal.

13. The portable light reflectance video system of claim 11 further comprising a multiplex circuit coupled to the processor, the display and the third video camera, the multiplex circuit provides video signals to the display comprising a sum of the output video signal from the processor and the third unfiltered video signal.

14. The portable light reflectance video system of claim 11 further comprising a multiplex circuit coupled to the processor and the display, the multiplex circuit provides video signals to the display of the output video signal from the processor which exceeds a predetermined threshold ratio value.

15. The portable light reflectance video system of claim 9 wherein the display displays the output video signal from the processor in gray scale.

16. The portable light reflectance video system of claim 9 wherein the first and second optical bandpass filters each have a bandwidth of 10 nm.

17. A method of viewing plant chlorophyll content for identifying early plant stress using a chlorophyll content imager, the method comprising the steps of:

detecting light from a light source having a first wavelength;

detecting light from the light source having a second wavelength;

providing a first video image of light reflected from a target plant having the first wavelength;

providing a second video image of light reflected from the target plant having the second wavelength;

providing a third video image of a first reflected percent of light, where the first reflected percent of light is determined by comparing the light reflected from the target plant having the first wavelength to the light detected from the light source having the first wavelength;

providing a fourth video image of a second reflected percent of light, where the second reflected percent of light is determined by comparing the light reflected from the target plant having the second wavelength from the light detected from the light source having the second wavelength;

providing a fifth video image as a ratio of the third video image to the fourth video image, wherein plant chlorophyll content is represented by the ratio of the third video image to the fourth video image; and displaying the fifth video image.

18. The method of claim 17 wherein a low ratio of the third video image to the fourth video image indicates a low level of plant stress, and a high ratio of the third video image to the fourth video image indicates a high level of plant stress.

19. The method of claim 17 wherein the first wavelength is 700 nm, and the second wavelength is 840 nm.

* * * * *